(12) United States Patent
Jung

(10) Patent No.: US 10,595,552 B2
(45) Date of Patent: Mar. 24, 2020

(54) PREPARATION OF MIXED TEA COMPOSITION COMPRISING ALOESWOOD

(71) Applicant: Jong Moon Jung, Seoul (KR)

(72) Inventor: Jong Moon Jung, Seoul (KR)

(*) Notice: Subject to any disclaimer, the term of this patent is extended or adjusted under 35 U.S.C. 154(b) by 70 days.

(21) Appl. No.: 16/057,723

(22) Filed: Aug. 7, 2018

(65) Prior Publication Data
US 2019/0216123 A1    Jul. 18, 2019

(30) Foreign Application Priority Data
Jan. 16, 2018  (KR) .......................... 10-2018-005316

(51) Int. Cl.
| | |
|---|---|
| *A61K 36/00* | (2006.01) |
| *A23L 33/105* | (2016.01) |
| *A23F 3/40* | (2006.01) |
| *A23F 3/18* | (2006.01) |
| *A61K 9/00* | (2006.01) |
| *A61K 36/899* | (2006.01) |
| *A61K 36/21* | (2006.01) |
| *A61K 36/64* | (2006.01) |
| *A61K 36/634* | (2006.01) |
| *A61K 36/718* | (2006.01) |
| *A61K 36/82* | (2006.01) |
| *A61K 36/835* | (2006.01) |

(52) U.S. Cl.
CPC .............. *A23L 33/105* (2016.08); *A23F 3/18* (2013.01); *A23F 3/405* (2013.01); *A61K 9/0095* (2013.01); *A61K 36/21* (2013.01); *A61K 36/634* (2013.01); *A61K 36/64* (2013.01); *A61K 36/718* (2013.01); *A61K 36/82* (2013.01); *A61K 36/835* (2013.01); *A61K 36/899* (2013.01); *A61K 2236/00* (2013.01)

(58) Field of Classification Search
None
See application file for complete search history.

(56) References Cited

U.S. PATENT DOCUMENTS 8,168,238 B2    5/2012 Wang et al.

FOREIGN PATENT DOCUMENTS

| | | | |
|---|---|---|---|
| CN | 105664213 A | * | 6/2016 |
| JP | H08126472 A | | 5/1996 |
| KR | 10-2010-0049965 A | | 11/2008 |
| KR | 10-0931880 B1 | | 12/2009 |
| KR | 10-1044641 B1 | | 6/2011 |
| KR | 10-2012-0010811 A | | 2/2012 |
| KR | 10-2017-0129176 A | | 11/2017 |
| WO | 2016/142745 A1 | | 9/2016 |

OTHER PUBLICATIONS

Dahham et al., "In vitro antimetastatic activity of Agarwood (*Aquilaria crassna*) essential oils against pancreatic cancer cells," Alexandria J. Medicine, 2016, pp. 141-150, vol. 52.
Regula Naef, "The volatile and semi-volatile constituents of agarwood, the infected heartwood of *Aquilaria* species: A review," Flavour Fragr. J., Jan. 10, 2011, pp. 73-89, vol. 26, John Wiley & Sons, Ltd.
Hashim et al., "*Aquilaria* spp. (*agarwood*) as source of heath beneficial compounds: A review of traditional use, phytochemistry and pharmacology," J. Ethnopharmacology, Jun. 22, 2016, pp. 331-360, vol. 189.

* cited by examiner

*Primary Examiner* — Qiuwen Mi
(74) *Attorney, Agent, or Firm* — Im IP Law; Chai Im; C. Andrew Im

(57) ABSTRACT

A method for preparing a mixed tea having an aloeswood. Each of the aloeswood tea, the green tea and the white tea is mixed with water in a weight ratio of 1:30 to 1:70. The aloeswood tea is brewed at a temperature of 90-100° C. for 30-80 seconds. The green tea is d brewed at a temperature of 80-85° C. for 30-80 seconds. The white tea is brewed at a temperature of 90-95° C. for 30-80 seconds. The aloeswood tea liquor, the green tea liquor and the white liquor are cooled to 5-15° C. The aloeswood liquor, the green tea liquor and the white tea liquor are mixed in a weight ratio of 1:2:1 to prepare a mixed raw water. The mixed raw water is mixed with mineral water in the weight ratio of 1:1,000 and heated. The solids are removed from the mixed raw water after the heating step.

1 Claim, No Drawings

PREPARATION OF MIXED TEA COMPOSITION COMPRISING ALOESWOOD

RELATED APPLICATION

This application claims priority from Korean Patent Application No. 10-2018-005316 filed Jan. 16, 2018, which is incorporated herein by reference in its entirety.

TECHNICAL FIELD

The present invention relates to a preparation of a mixed tea composition comprising aloeswood, more specifically, to the preparation of the mixed tea composition comprising aloeswood, for helping in hemostatic action, alleviating menstrual pain, and improving eye diseases.

BACKGROUND OF THE INVENTION

Aloeswood is a resin part filled after which is produced by defense action when the aloeswood tree has damaged by external stimuli, which is an evergreen arbor of Aquilaria genus belonging to Thymeleaceae which grows in Southeast Asia region of subtropical climate. More specifically, the damages of the aloeswood occur on the xylem due to the external stimulus when the stems or branches of the aloeswood are broken or bended due to climates such as storms, strong winds, etc., or when noxious insects, ants, birds, etc. dig up the woody layer of the aloeswood tree to build a nest, or beasts such as a tiger, leopard, etc. scratch the aloeswood tree with sharp claws and breaks the branches, and the like, while fighting against each other, or marking its territory. Then, the aloeswood tree itself makes the resin by means of cells around the damage, and the resin fills the damaged site, and this is called as the aloeswood. This aloeswood plays a role as a defense membrane for treating the damage and protecting the damaged site from the external infection. Such an aloeswood is slowly formed and deposited on the xylem over a long period from at least 3 years to 100 years. Although the aloeswood was dead, it is remained in the state of having the aloeswood in the xylem while maintaining the shape of the tree, or the tree is fallen down and buried in the earth while the tree is dying, and thus, the xylem is rotting away and the aloeswood being the resin mass remains as it is.

The aloeswood produced as above has an effect of fragrance or scent which is clearly differentiated from other aromatic plants, and thus, has been treated as the important fragrance or medicinal for a long time. Also, since the aloeswood is very unique when it burns in a fire and gives fragrant scent making the feeling good when anyone smells, it was divided into three big fragrances in the world, and is also a precious substance which is traded at a higher price than gold because of the scarcity of production in the world.

In the herbal medicinally, the nature of the aloeswood is non-toxic, spicy and warm, and its efficacies such as aromatic fragrance, warming pain and scattering cold, lowering the vitality (energy) and warming the inside of the body, protecting kidney and absorbing lung vitality, and warning spleen and stomach and lessening vomiting are known. Also, in Dong-Eui-Bo-Gam by Huh Joon in Chosun Dynasty, it is described that <The aloeswood controls the parts swollen by wind, water or poison, removes wrong vitality, and stops heartache and stomachache. In the boiling decoction, the aloeswood is mixed as a powder after milling or grinding it and drunken, and in a tablet or powder, the aloeswood is finely milled separately and then is eaten>, and in Ben Cao Gang Mu (Compendium of Materia Medica) by L I Shizhen, there is a record stating that <The aloeswood corrects the upsurge of energy, regulates and warms the internal organs, and treats the pain by letting the energy pass.>, and based on this efficacy, it has been known to have been used for vomiting, diarrhea, constipation, and backache syndrome, and the like.

According to a paper (thesis) by Hashim, et al. on 2016, in South-East Asia countries such as Vietnam, Indonesia, Malaysia, etc., and East-North Asia countries such as Korea, China, Japan, etc., it is said that the fragrance of the aloeswood was smelled or the aloeswood was eaten for the treatment of anti-inflammation, arthritis, malaria, vomiting, headache, asthma, stabilizer, analgesics, antispasmodics, etc., and the pharmacological effect of the aloeswood has been reported to have the effect such as anti-inflammation, anti-cancer, antipyretic, antispasmodic, analgesic, antioxidant, anti-allergic, and the like (Journal of Ethonopharmacology, 189, 331~360). Meanwhile, according to a paper by Naef on 2011, the plant of Aquilaria genus includes sesqueterpene, monoterpene, terpene series, etc. (Flavour and Gragrance Journal, 26, 73-89); according to a paper by Dahham, et al. on 2016, an anti-cancer activity was ascertained in pancreatic cells of essential oil obtained from a vapor distillation-extraction method in the plant of Aquilaria genus (Alexandria Journal of Medicine, 52, 141~150); and U.S. Pat. No. 8,168,238 introduces a method for preparing an extract of Aquilaria genus including curcubitacin component, etc., representing effect for preventing or treating cancer, and the use thereof.

Meanwhile, upon reviewing the technologies regarding the aloeswood, Korean Patent Application No. 10-2008-0098571 relates to a method for preparing the aloeswood, which comprises steps for cutting a fragrant tree or oak tree according to the necessary use; for drying the resultant cut tree which was cut for fitting the purpose in an air-blowing and drying room having an internal temperature of 90~95° C. during 2 hours and 30 minutes~3 hours and 30 minutes; for high pressure-impregnating the mixed water mixing the concentrated deep water and valley water concentrated inside the wood dried in the drying room in a ratio of 3:1; for drying the wood impregnated with the mixed water in the air-blowing and drying room again; for repeatedly performing the step of high pressure-impregnation and drying procedure; for inspecting the density and flagrance of the tree completed by the repetitive high-pressure impregnation and drying steps to separate the tree passed the conditions, said method is a technology to prepare the aloeswood having high fragrance and density in a short period by cutting the flagrance tree or oak tree in various sizes, wherein the aloeswood made by the above has effects being able to be supplied and used in various fields throughout the industries such as sculpture, materials for decorating car interior, exterior materials of mobile phone, etc. as well as high-grade incense.

Also, Korean Patent Application No. 10-2009-0080235 relates to herbal drink comprising an aloeswood, Northern bamboo, milkwort and Zizyphus spinosi, and a method for preparing the same, and a functional herbal drink for alleviating heart diseases continuously without making any side effect, and the method thereof.

The present invention relates a method for preparing beverages which have effects reducing the total cholesterol concentration without any side effect by using the herbal medicine ingredient as a main ingredient, preventing the heart attack due to the myocardial infarction by clearing the heart blood vessel, and relaxing depression by resolving insomnia, which is the method for preparing a herbal drink (oriental medicine beverage) comprising aloeswood, Sasa borealis, milkwort and Zizyphus spinosi, which comprises the primary mixing step mixing 100 to 150 parts by weight of Sasa borealis, 150 to 200 parts by weight of milkwort and 100 to 150 parts by weight of Zizyphus spinosi in relation to 100 parts by weight of aloeswood; the secondary mixing step for mixing the mixture with 1.5 to 6 times of parts by weight of water in relation to the total weight of the mixture; and a distillation step by heating the container and passing the vapor emitted to a vapor outlet through a cooler to obtain a distillation liquor.

Accordingly, if a technique that combines aloeswood with the above-mentioned efficacy to a tea that can be taken at any time, and combines the fragrance of aloeswood with the tea, simultaneously with maintaining the original flavor and taste of the tea, can be developed, it will be a technology that can help a lot of users, since the flavor and taste of the tea can be continuously enjoyed.

OBJECT AND SUMMARY OF THE INVENTION

Technical Problem

The present invention is created for overcoming the above-mentioned problems, and provides a method for preparing a mixed tea comprising aloeswood by preparing the aloeswood into the mixed tea for helping anti-allergy, spasmolytic, analgesic and relaxing effects, recovery of physical strength and/or health promotion to add the pharmacological performance useful for a human as well as to improve the total preference by not lowering the taste which makes a human easily drink it.

Means for Resolving the Problem

The present invention provides a method for preparing a mixed tea comprising an aloeswood, which comprises:

a brewing step of an aloeswood tea, which comprises mixing the aloeswood tea with water in a weight ratio of 1:30 to 1:70 and then brewing it at a temperature of 90 to 100° C. for 30 to 80 seconds;

a brewing step of a green tea, which comprises mixing the green tea with water in a weight ratio of 1:30 to 1:70 and then brewing it at a temperature of 80 to 85° C. for 30 to 80 seconds;

a brewing step of a white tea, which comprises mixing the white tea with water in a weight ratio of 1:30 to 1:70 and then brewing it at a temperature of 90 to 95° C. for 30 to 80 seconds;

a cooling step which comprises cooling the aloeswood liquor, the green tea liquor and the white liquor finished by said brewing steps, into 5 to 15° C.;

a preparation step of raw water, which comprises mixing the aloeswood liquor, the green tea liquor finished by the cooling step in a weight ratio of 1:2:1 to prepare raw water of the mixed tea in which the aloeswood tea, the green tea and the white tea are mixed therein;

a step for heating in boiling water, which comprises mixing the mixed raw water with mineral water in the weight ratio of 1:1,000 after finishing the preparation step of the raw water; and a removal step of solids, which comprises removing a sediment, float or debris after finishing the step for heating in boiling water.

Advantageous Effects

The preparation method of the mixed tea comprising the aloeswood according to the present invention has the effect which makes that one can easily take the aloeswood which is helpful in anti-allergy, spasmolytic, analgesic and relaxing effects, recovery of physical strength, health promotion, and the like, without lowering the taste which make a human easily drink it.

DETAILED DESCRIPTION OF THE EMBODIMENTS

Hereinafter, the present invention will be explained in detail.

The present invention provides a method for preparing a mixed tea comprising an aloeswood, which comprises:

a brewing step of an aloeswood tea, which comprises mixing the aloeswood tea with water in a weight ratio of 1:30 to 1:70 and then brewing it at a temperature of 90 to 100° C. for 30 to 80 seconds;

a brewing step of a green tea, which comprises mixing the green tea with water in a weight ratio of 1:30 to 1:70 and then brewing it at a temperature of 80 to 85° C. for 30 to 80 seconds;

a brewing step of a white tea, which comprises mixing the white tea with water in a weight ratio of 1:30 to 1:70 and then brewing it at a temperature of 90 to 95° C. for 30 to 80 seconds;

a cooling step which comprises cooling the aloeswood liquor, the green tea liquor and the white liquor finished by said brewing steps, into 5 to 15° C.;

a preparation step of raw water, which comprises mixing the aloeswood liquor, the green tea liquor finished by the cooling step in a weight ratio of 1:2:1 to prepare raw water of the mixed tea in which the aloeswood tea, the green tea and the white tea are mixed therein;

a step for heating in boiling water, which comprises mixing the mixed raw water with mineral water in the weight ratio of 1:1,000 after finishing the preparation step of the raw water; and a removal step of solids, which comprises removing a sediment, float or debris after finishing the step for heating in boiling water.

The brewing step of an aloeswood tea according to the present invention comprises mixing the aloeswood tea with water in a weight ratio of 1:30 to 1:70 and then brewing it at a temperature of 90 to 100° C. for 30 to 80 seconds.

Herein, the aloeswood tea is made to be drunken by the aloeswood which is produced by hardening a resin on the aloeswood tree, and any ordinary aloeswood tea of the related art having such a purpose can be used.

In particular, the aloeswood tea according to the present invention is the best heavenly fragrance and is rich in monoterpene, terpene, and sesquiterpene-based substances, and thus is helpful in anti-allergy, spasmolytic, analgesic and relaxing effects, recovery of physical strength, health promotion, etc., and also provides the pharmacological property such as an anti-cancer effect.

In a particular embodiment, although the aloeswood tea liquor according to the present invention obtained from the brewing step of the aloeswood tea may be obtained by heating it in boiling water at the temperature range of 35 to 45° C. for 45 to 50 hours, it can be selected and used by the user's choice.

The brewing step of a green tea according to the present invention comprises mixing the green tea with water in a weight ratio of 1:30 to 1:70 and then brewing it at a temperature of 80 to 85° C. for 30 to 80 seconds.

Herein, although any of the green teas may be used if it is any green tea commonly used in the art, preferably green tea leaves, green tea powder or a mixture thereof may be used, and more preferably green tea leaves may be used.

Specifically, as the green tea according to the present invention, an extract extracted from the green tea, that is, the green tea extract may be used.

At this time, the green tea extract can provide an antimicrobial effect, preferably antibacterial effect on periodontitis (Haemophilus actinomycetemcomitans) and a deodorizing effect by providing a detoxifying action and the sterilizing action because of a tannin component contained in the green tea extract, a strong deodorizing effect on the malodorous component in the oral cavity.

The brewing step of a white tea according to the present invention comprises mixing the white tea with water in a weight ratio of 1:30 to 1:70 and then brewing it at a temperature of 90 to 95° C. for 30 to 80 seconds;

Herein, the white tea is a tea made by drying the young shoots of the downy tea as it is without washing or rubbing it, and the young shoots are covered with white fluff so that the tea has a silver luster, clear fragrance and fresh taste.

Such white tea not only removes fat, smoothes urination and cleanses the intestines, but, also is good for diabetic patients and is used as medicinal herb because it has a heat-releasing effect in summer.

The cooling step according to the present invention comprises cooling the aloeswood tea liquor, the green tea liquor and the white tea liquor finished by the brewing steps into 5 to 15° C.

Herein, the method may further comprise a solid-removal step removing sediments, suspensions, or debris in the cooled aloeswood tea liquor, the green tea liquor, and white tea liquor at the end of the cooling step.

The preparation step of raw water according to the present invention comprises mixing the aloeswood tea liquor, the green tea liquor and the white tea liquor in a weight ratio of 1:2:1.

The step for heating in boiling water according to the present invention comprises mixing the raw water of mixed tea with mineral water in the weight ratio of 1:1,000 after finishing the preparation step of the raw water and then heating it in boiling water at the temperature of the range of 60 to 65° C. for 45 to 50 hours.

Herein, any mineral water may be used if it is the conventional mineral water in the art, including minerals.

Specifically, the mineral water used according to the present invention can be the purified water. In this case, the purified water to be used may use the purified water containing minerals, for example, the purified water containing mineral ions of zinc, copper, silver, iron and tin, which assists to alcoholysis or a human metabolism, and an ionization of the mineral is made by the high voltage electrolysis, and is preferable to contain the mineral ions in the amounts of 300 ppm or less.

The removal step of solids according to the present invention comprises removing precipitates, floats or debris after finishing the step for heating in boiling water.

The preparation method of the mixed tea comprising aloeswood according to the present invention may further comprise one or more kinds of adducts according to the following specific embodiments.

In a specific embodiment, in the preparation method of the mixed tea comprising aloeswood according to the present invention, the raw water of the mixed tea used in the step for heating in boiling water, preferably the raw water obtained after finishing the preparation step of raw water of the mixed tea may further comprise 1 to 20 parts by weight of a Cockscomb paste, based on 100 parts by weight of the raw water of the mixed tea.

The Cockscomb paste refers to the paste prepared by using a Common Cockscomb.

The Cockscomb paste is not particularly limited as long as it is a paste of the conventional Cockscomb, but it is preferable to use one obtained by pulverizing flowers, fruits, leaves, seeds or a mixture of the Cockscomb, or a fermentation broth of the lyophilized Cockscomb, a Cockscomb liquor, a Cockscomb extract or a mixture of at least one or more being selected from them.

Herein, it is recommended that particles of the Cockscomb paste can be pulverized to an average size of 0.5 to 5 mm, and more preferably to the size of about 4 mm. The pulverization may be carried out by using a pulverizer commonly used for pulverizing medicinal plants, and the pulverized material obtained by the pulverization may be filtered through a mesh to produce the Cockscomb paste with a constant size.

In addition, the Cockscomb fermentation liquor comprises one prepared by mixing the seeds, fruit, flowers, leaves, stem of Cockscomb or a mixture of at least one or more being selected from them with sugar, preferably mixing the Cockscomb with sugar in a weight ratio of 3:7 to 7:3, preferably in a weight ratio of about 5:5, and then aging the mixture.

In a specific embodiment, the Cockscomb paste according to the present invention is preferably used as one prepared by the following steps:

a solvent spraying step for spraying the solvent comprising 20 to 30% by weight of ethyl alcohol and 70 to 80% by weight of distilled water on the Cockscomb;

the primary drying step for exposing the Cockscomb obtained after finishing the solvent-spraying step under the light for 3 to 6 days to dry it;

a distilled water-spraying step for spraying the distilled water to the Cockscomb dried by the primary drying step;

the secondary drying step for exposing the Cockscomb obtained after finishing the distilled water-spraying step to light for 1 to 2 days to dry it; and a pulverizing step for pulverizing the Cockscomb obtained after finishing the secondary drying step to obtain the powder of the Cockscomb.

Herein, the Cockscomb used in the preparation step of the Cockscomb paste is an annual plant of Amaranthaceae, Centriole Order, Dicotyledoneae, and the Cockscomb is called as Gaekwanhwa because the shape of its flower resembles a comb of chicken and is characterized by having a cold feature and a bitter taste. It is known that Cockscomb is effective to relieve inflammation and to stop bleeding and diarrhea by touching a liver and large intestine due to its cool and bitter taste features. In addition, it is recorded in a Botanical list that the roasted seeds of Cockscomb are good to relieve leucorrhea of a woman or the case that menses, diarrhea, etc. is not stopped.

Preferred Cockscomb include seeds, flowers, leaves or stems of the Cockscomb, or mixtures thereof.

In a specific embodiment, the Cockscomb used in the step for preparing the Cockscomb according to the present invention may further include a separate pretreatment procedure to further enhance the Cockscomb effect of the Cockscomb paste. As an example of this, the step for spraying said solvent may use the Cockscomb experiencing the drying step for drying the Cockscomb under the natural or hot-air; the primary roasting step for roasting the Cockscomb after finishing the drying step; the primary pulverizing step for pulverizing the Cockscomb with a crusher after finishing the primary roasting step; the secondary roasting step for roasting the Cockscomb secondly after finishing the primary pulverizing step; and the secondary pulverizing step for pulverizing the Cockscomb with the crusher after finishing the secondary roasting step.

Herein, the crusher used in the pulverization step is not particularly limited as long as it is a crusher commonly used in the art, and the powder of the Cockscomb pulverized in the pulverizing step is sorted by using a mesh, etc. so that the particle size of final Cockscomb is 0.5~5 mm.

In another specific embodiment, an enzyme addition step for adding one enzyme selected from lipoxygenase and hydroperoxide lyase may be further included in the end of the secondary drying step included in the Cockscomb paste preparation step, the used amounts may be preferably 0.1 to 0.2 parts by weight, based on 100 parts by weight of the Cockscomb. In this case, one enzyme selected from lipoxygenase and hydroperoxide lyase can prevent the loss of the intrinsic flavor and taste of the Cockscomb and also enhance the flavor component such as aldehyde ketone, etc.

In another specific embodiment, an antisepsis step for injecting carbon dioxide gas or nitrogen gas which is colorless and odorless, inert and harmless to the human body in the closed space to prevent the decomposition the Cockscomb paste by preventing the re-penetration of moisture by the gas impregnated in the tissue of the Cockscomb paste to be dried may be included in the end of the pulverizing step included in the step for preparing the Cockscomb paste.

In another specific embodiment, in the preparation method of the mixed tea comprising aloeswood according to the present invention, the raw water of the mixed tea used in the step for heating in boiling water, preferably the raw water of the mixed tea after finishing the step for preparing the mixed tea may further include 1 to 20 parts by weight of Rhemannia extract, based on 100 parts by weight.

In this case, the Rehmania extract refers to a substance extracted from Rehmania glutinosa.

Rehmannia glutinosa is a plant of Scrophularia root order, that is, a perennial herbaceous plant of Phrymaceae, which is originated from China and usually refers to roots, and the roots of Rehmannia glutinosa taken in autumn are thick and long, like a small sweet potato and have scabrous knots.

It has been reported that such chemical components of Rehmannia glutinosa include iridoid and various useful components such as Catalposide, acteoside, martynosides, forsythiaside and phenolic glycoside. These components have been reported to have an enhancement of immune activity, hypoglycemic effect, anti-aging, anti-gastric ulcer and gastric mucosal protection effect, anti-cancer effect, and strengthening the gums (gingiva). And the root of Rehmannia glutinosa contains eleven kinds of amino acids including a large amount of sugar and arginines such as 6% of glucose, 32% of stachyose, etc.

In another specific embodiment, the preparation method of the mixed tea including the aloeswood according to the present invention may further comprise 1 to 20 parts by weight of Forsythia fruit extract, based on 100 parts of weight of the raw water of mixed tea after finishing the step for preparing the raw water of mixed tea.

In this case, the Forsythia fruit extract refers to the substance extracted from the Forsythia fruit.

The forsythia fruit means a fruit of Korean forsythia which is a plant of Oleaceae, and is usually used in the dried state after collecting fruits when they are firstly ripened or fully ripened and then drying them under the sun.

In particular, the forsythia fruit is widely used in oriental medicine mainly as antipyretic, detoxification, drainage, anti-inflammatory or diuretic agent and used with other medicinal stuff in purulent disease, turgescence, gonorrhea, menstrual irregularity, diuresis, hemorrhoids, tuberculosis, scabies, detoxification and the like. In addition, the extracts or degradation products of the forsythia fruit are known to have antimicrobial action, and the flowers contain quercetin, glucoside, rutin, and ascorbic acid, which are pigmented glycosides, and are very effective in the beauty of women such as antioxidants, antibacterial agents, anti-inflammation, inhibition of elastin digesting enzyme, and the like.

Therefore, the extract of forsythia fruit according to the present invention has a high tyrosinase activity-inhibitory effect and a high melanin production inhibitory effect, and thus, can provide an excellent whitening effect.

In another specific embodiment, in the method for preparing the mixed tea containing the aloeswood according to the present invention, the raw water of mixed tea used in the step for heating in boiling water, preferably the raw water of mixed tea after finishing the step for preparing the raw water may further include 1 to 20 parts of weight of Golden thread extract, based on 100 parts by weight of the raw water of the mixed tea.

In this case, the Golden thread extract refers to a substance extracted from Golden thread.

The Golden thread is a perennial plant of Buttercup ranunclaceae and is called Golden thread because of yellow roots in series and also called as Jeffersonia dubia in a private house. Leaves are egg-shaped or triangular and split like feathers, and grow in high mountain areas such as Sichuan, Hubei, Guizhou and Shaanxi province in central China, or cultivated as an herb.

Since the roots of such Golden thread contain berberine and alkaloids, they are often used for yellow, especially golden dyeing, but the berberine has a hypotensive action, cardiotonic action, antipyretic action, antibacterial action, sedative action and anti-inflammation action, and can kill dermatophyte or Candida albicans. Therefore, in the oriental medicine, it is used as a sedative agent or an anti-inflammatory agent, and the roots of it are used in heart palpitations, mental anxiety, colic, diarrhea, dysentery, etc.

In another specific embodiment, the method for preparing the mixed tea comprising aloeswood according to the present invention may further comprise 1 to 20 parts by weight of a grain fermented product, based on 100 parts by weight of the raw water of mixed tea used in the step for heating in boiling water, preferably the raw water of mixed tea after finishing the raw water-preparation step.

In another specific embodiment, the method for preparing the mixed tea comprising aloeswood according to the present invention may further comprise 1 to 50 parts by weight of a grain fermented product, based on 100 parts by weight of the raw water of mixed tea used in the step for heating in boiling water, preferably the raw water of mixed tea after finishing the raw water-preparation step.

Herein, the grain fermented product is one obtained by fermenting a grain with yeast, leaven and/or acetic acid bacteria as the fermenting bacteria, and includes a liquor phase and solid phase (powder, lyophilized (freeze-dried) product).

In addition, the type of the grain is not limited, but preferably includes rice, rye flour, whole wheat flour, oats, glutinous rice, and the like.

Hereinafter, the present invention will be described in detail with reference to examples. However, the following examples are for illustrative purpose only and are not intended to limit the scope of the present invention.

Example 1

1 g of Aloeswood tea and 50 g of water were mixed and then an aloeswood tea liquor was prepared at the temperature of about 95° C. for 60 seconds.

Then, 1 g of green tea and 50 g of water were mixed, and a green tea liquor was prepared by brewing it at a temperature of about 83° C. for 60 seconds.

Then, 1 g of white tea and 50 g of water were mixed, and then a white tea liquor was prepared by brewing it at a temperature of about 93° C. for about 50 seconds.

Then, the brewed aloeswood tea liquor, green tea liquor and white tea liquor were cooled to about 10° C. Then, the aloeswood tea liquor, green tea liquor and white tea liquor after finishing the cooling step were mixed in a weight ratio of 1:2:1 to prepare the raw water of mixed tea in which the aloeswood tea liquor, green tea liquor and white tea liquor are mixed.

Then, 10 g of the mixed raw water and 10,000 g of mineral water were mixed, and the mixture was heated in boiling water at a temperature of 63° C. for 48 hours.

Then, the mixed tea was prepared by removing the scraps, etc. from the mixture which was heated in boiling water.

Cockscomb Paste Preparation 1

The mixed solvent of 25 g of ethyl alcohol and 75 g of the distilled water was sprayed on 500 g of Cockscomb flower and then the Cockscomb flower was dried by exposing it to light for 4 days.

Then, 100 g of the distilled water was sprayed on the dried Cockscomb flower, and then the Cockscomb flower was exposed to light for 1.5 hours to dry.

Then, the Cockscomb flower was pulverized using a crusher, and sorted with a mesh to prepare the Cockscomb paste having an average particle size of 0.5 to 5 mm.

Cockscomb Paste Preparation 2

The same procedure as in the Cockscomb paste preparation 1 was practiced, except for using the pulverized Cockscomb flower obtained by drying 500 g of Cockscomb flower with a far-infrared drier at a temperature of 65° C. for 7 hours, and then the $1^{st}$ roasting it at 45° C. for 2 minutes, the $1^{st}$ pulverizing it using the crusher, and the $2^{nd}$ roasting it again at 90° C. for 2 minutes, and then pulverizing it.

Cockscomb Paste Preparation 3

The same procedure as in the Cockscomb paste preparation 2 was practiced, except for adding 0.5 g of lipoxygenase after exposing it to light to dry.

Cockscomb Paste Preparation 4

The same procedure as in the Cockscomb paste preparation 1 was practiced, except for pulverizing it using the crusher, and then impregnating it with the nitrogen gas in the closed space at 50° C. for 10 hours.

Example 2

The same procedure as in Example 1 was practiced, except for mixing 1 g of the Cockscomb paste prepared by mixing the Cockscomb paste preparation 1 with 10 g of the raw water of mixed tea and heating it in boiling water by placing it in the mineral water.

Example 3

The same procedure as in Example 1 was practiced, except for mixing 1 g of the Cockscomb paste prepared according to the Cockscomb paste preparation 2 with 10 g of the raw water of mixed tea and heating it in boiling water by placing it in the mineral water.

Example 4

The same procedure as in Example 1 was practiced, except for mixing 1 g of the Cockscomb paste prepared by mixing the Cockscomb paste preparation 3 with 10 g of the raw water of mixed tea and heating it in boiling water by placing it in the mineral water.

Example 5

The same procedure as in Example 1 was practiced, except for mixing 1 g of the Cockscomb paste prepared by mixing the Cockscomb paste preparation 4 with 10 g of the raw water of mixed tea and heating it in boiling water by placing it in the mineral water.

Example 6

The same procedure as in Example 1 was practiced, except for mixing 1 g of the Rhemannia extract with 10 g of the raw water of mixed tea and heating it in boiling water by placing it in the mineral water.

Example 7

The same procedure as in Example 1 was practiced, except for mixing 1 g of the Forsythia fruit extract with 10 g of the raw water of mixed tea and heating it in boiling water by placing it in the mineral water.

Example 8

The same procedure as in Example 1 was practiced, except for mixing 1 g of the Goldthread extract with 10 g of the raw water of mixed tea and heating it in boiling water by placing it in the mineral water.

Example 9

The same procedure as in Example 1 was practiced, except for mixing 3 g of the fermented rye flour with 10 g of the raw water of mixed tea and heating it in boiling water by placing it in the mineral water.

Example 10

The same procedure as in Example 1 was practiced, except for adding all of adducts of Examples 5 to 9 and heating it in boiling water.

Experiment 1

Sensory evaluations of the mixed teas prepared according to the examples in terms of sweet taste, bitter taste, sour taste and overall preference were practiced, and the results are shown in Table 1.

TABLE 1

| | Sweetness | Bitter taste | Sour taste | Preference |
|---|---|---|---|---|
| Example 1 | 1.5 | 1.2 | 2.4 | 2.70 |
| Example 2 | 1.5 | 1.2 | 2.4 | 2.75 |
| Example 3 | 1.3 | 1.2 | 2.3 | 2.80 |
| Example 4 | 1.7 | 1.4 | 2.5 | 2.71 |
| Example 5 | 1.6 | 1.6 | 2.1 | 2.63 |

TABLE 1-continued

|  | Sweetness | Bitter taste | Sour taste | Preference |
|---|---|---|---|---|
| Example 6 | 1.9 | 1.0 | 2.0 | 2.96 |
| Example 7 | 1.5 | 1.2 | 2.3 | 2.81 |
| Example 8 | 1.6 | 1.3 | 2.5 | 2.71 |
| Example 9 | 1.6 | 1.6 | 2.3 | 2.73 |
| Example 10 | 1.8 | 1.5 | 2.1 | 2.92 |

As shown in Table 1, Examples 1 to 10 using the method for preparing the mixed tea comprising aloeswood showed a high sweet taste, low bitter taste and high overall preference.

Experiment 2

50 people of the 20s (twenties) and 40s (forties) were selected, and a total of 30 people were selected for each of 10 persons so that the same ages are distributed, and allowed to pour each of the mixed teas prepared according to the Examples into the coffee cup and let them drink the teas at an interval of ten minutes, and then the taste, flavor and preference of them were divided and evaluated using the 9-point scale method.

The results are shown in Table 2.

TABLE 2

|  | Taste | Flavor | Preference |
|---|---|---|---|
| Example 1 | 8.5 | 8.1 | 8.1 |
| Example 2 | 8.4 | 8.5 | 8.4 |
| Example 3 | 8.2 | 8.1 | 8.3 |
| Example 4 | 8.4 | 8.2 | 8.5 |
| Example 5 | 8.3 | 8.2 | 8.1 |
| Example 6 | 8.6 | 8.8 | 8.6 |
| Example 7 | 8.4 | 8.2 | 8.3 |
| Example 8 | 8.4 | 8.2 | 8.4 |
| Example 9 | 8.3 | 8.3 | 8.1 |
| Example 10 | 8.5 | 8.7 | 8.5 |

As shown in Table 2, Examples 1 to 10 using the method for preparing the mixed tea comprising aloeswood showed high taste, flavor and overall preference.

As described above, people having ordinary skill in the art to which the present invention belongs will understand that the present invention may be practiced in other specific forms without departing from the technical spirit or essential characteristics thereof. It is therefore to be understood that all the examples described above are exemplary and non-restrictive. The scope of the present invention should be construed that all changes and alterations derived from the meaning and scope of the following claims and the equivalents are included in the scope of the present invention.

The invention claimed is:

1. A method for preparing a mixed tea comprising an aloeswood, which comprises steps of:
    brewing an aloeswood tea liquor, which comprises mixing 1 gram of the aloeswood tea with 50 grams of water and then brewing the aloeswood tea liquor at a temperature of 95° C. for 60 seconds;
    brewing a green tea liquor, which comprises mixing 1 gram of a green tea with 50 grams of water and then brewing the green tea liquor at a temperature of 83° C. for 60 seconds;
    brewing white tea liquor, which comprises mixing 1 gram of a white tea with 50 grams of water and then brewing the white tea liquor at a temperature of 93° C. for 50 seconds;
    cooling the aloeswood tea liquor, the green tea liquor and the white tea liquor to 10° C.;
    removing a sediment, float or debris from the cooled aloeswood tea liquor, the cooled green tea liquor and the cooled white tea liquor after the cooling step;
    mixing the aloeswood liquor, the green tea liquor and the white tea liquor cooled to 10° C. in a weight ratio of 1:2:1 to prepare a mixed raw water in which the aloeswood tea, the green tea and the white tea are mixed therein;
    heating 10 grams of the mixed raw water mixed with 10,000 grams of a mineral water, 1 gram of cockscomb paste, 1 gram of rhemannia extract, 1 gram of forsythia extract, 1 gram of goldthread extract and 3 grams of fermented rye flow extract;
    removing the sediment, float or debris after the heating step; and
    wherein the cockscomb paste prepared by sequentially:
        drying a cockscomb flower for 7 hours at 65° C. using a far-infrared drier;
        roasting the dried cockscomb flower for 2 minutes at 45° C.;
        pulverizing the roasted cockscomb flower using a pulverizer;
        roasting the pulverized cockscomb flower for 2 minutes at 90° C.;
        spraying a mixed solvent comprising 25 grams of ethyl alcohol and 75 grams of distilled water to 500 grams of the roasted, pulverized cockscomb flower;
        drying the cockscomb flower by exposing it to a light for four days;
        spraying 100 grams of distilled water to the dried cockscomb flower and exposing it to the light for 1.5 days;
        adding 0.5 gram of lipoxygenase to the dried cockscomb flower and pulverizing a resulting paste using the pulverizer; and
        impregnating the pulverized resulting pasted with a nitrogen gas in a closed space for 10 hours at 50° C. to provide the cockscomb paste.

\* \* \* \* \*